United States Patent
Bienvenu et al.

(10) Patent No.: US 10,500,382 B2
(45) Date of Patent: Dec. 10, 2019

(54) DRUG-FILLED STENTS WITH FILAMENTS FOR INCREASED LUMEN SURFACE AREA AND METHOD OF MANUFACTURE THEREOF

(71) Applicant: Medtronic Vascular, Inc., Santa Rosa, CA (US)

(72) Inventors: Ryan Bienvenu, Santa Rosa, CA (US); Justin Peterson, Santa Rosa, CA (US); Stefan Tunev, Santa Rosa, CA (US); Michael Harms, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 16 days.

(21) Appl. No.: 15/808,610

(22) Filed: Nov. 9, 2017

(65) Prior Publication Data
US 2018/0126135 A1 May 10, 2018

Related U.S. Application Data

(60) Provisional application No. 62/420,473, filed on Nov. 10, 2016.

(51) Int. Cl.
*A61F 2/88* (2006.01)
*A61F 2/86* (2013.01)
(Continued)

(52) U.S. Cl.
CPC ............. *A61M 31/002* (2013.01); *A61F 2/86* (2013.01); *A61F 2/88* (2013.01); *A61L 31/022* (2013.01);
(Continued)

(58) Field of Classification Search
CPC ...... A61F 2/86; A61F 2/88; A61F 2/89; A61F 2/90; A61F 2/91
See application file for complete search history.

(56) References Cited

U.S. PATENT DOCUMENTS

| 4,800,882 A | 1/1989 | Gianturco |
| 4,886,062 A | 12/1989 | Wiktor |

(Continued)

FOREIGN PATENT DOCUMENTS

| WO | 2008/063780 A2 | 5/2008 |
| WO | 2008/106223 A1 | 9/2008 |
| WO | 2014/162902 A1 | 10/2014 |

OTHER PUBLICATIONS

Lee, Jung-Jin et al., "Evaluation of Effect of Galvanic Corrosion Between Nickel-Chromium Metal and Titanium on Ion Release and Cell Toxicity" J Adv Prosthodont 2015;7:172-7, pp. 1-6.

(Continued)

*Primary Examiner* — Suba Ganesan
(74) *Attorney, Agent, or Firm* — Medler Ferro Woodhouse & Mills PLLC

(57) ABSTRACT

A stent including a hollow wire formed into a stent pattern. The hollow wire includes an outer member having an outer surface and an inner surface, a lumen extending longitudinally within the hollow wire, at least one opening extending from the outer surface of the outer member to the lumen, and a plurality of filaments extending longitudinally within the lumen. The plurality of filaments increases the amount of surface area available for tissue in-growth within the lumen. Each filament of the plurality of filaments is spaced from adjacent filaments of the plurality of filaments, and the spacing between adjacent filaments of the plurality of filaments is configured to permit tissue in-growth between the adjacent filaments.

19 Claims, 5 Drawing Sheets

(51) Int. Cl.
*A61M 31/00* (2006.01)
*A61L 31/02* (2006.01)
*A61L 31/16* (2006.01)
*A61L 31/18* (2006.01)
*A61F 2/915* (2013.01)

(52) U.S. Cl.
CPC ............... *A61L 31/16* (2013.01); *A61L 31/18* (2013.01); *A61F 2002/91575* (2013.01); *A61F 2230/0006* (2013.01); *A61F 2240/001* (2013.01); *A61F 2250/0068* (2013.01); *A61F 2250/0098* (2013.01)

(56) References Cited

U.S. PATENT DOCUMENTS

| | | | |
|---|---|---|---|
| 5,019,090 | A | 5/1991 | Pinchuk |
| 5,133,732 | A | 7/1992 | Wiktor |
| 5,782,903 | A | 7/1998 | Wiktor |
| 6,136,023 | A | 10/2000 | Boyle |
| 7,167,746 | B2 | 1/2007 | Pederson |
| 7,682,388 | B2 | 3/2010 | Rea |
| 2007/0244536 | A1 | 10/2007 | Pederson |
| 2007/0270942 | A1 | 11/2007 | Thomas |
| 2009/0023004 | A1 | 1/2009 | Pederson |
| 2009/0187254 | A1 | 7/2009 | Deal et al. |
| 2010/0303882 | A1 | 12/2010 | Cantrell et al. |
| 2011/0040371 | A1* | 2/2011 | Hanssen ............... A61F 2/88 623/1.22 |
| 2011/0245904 | A1 | 10/2011 | Pacetti et al. |
| 2011/0251668 | A1 | 10/2011 | Thompson et al. |
| 2012/0067103 | A1 | 3/2012 | Bienvenu et al. |
| 2013/0274864 | A1* | 10/2013 | Bienvenu ............... A61L 31/16 623/1.16 |
| 2015/0297803 | A1 | 10/2015 | Pulugurtha |

OTHER PUBLICATIONS

Devine, D.M. et al., "Tissue Reaction to Implants of Different Metals: A Study Using Guide Wires in Cannulated Screws" www.ecmjournal.org, European Cells and Materials, vol. 18 2009 (pp. 40-48), pp. 40-48.

Sansone, Valerio et al., "The Effects on Bone Cells of Metal Ions Released From Orthopaedic Implants. A Review" Clinical Cases in Mineral and Bone Metabolism 2013; 10(1): 34-40.

Acevedo, Daniel, MD et al., "Mixing Implants of Differing Metallic Composition in the Treatment of Upper-Extremity Fractures" www.healio.com/orthopedics/journals/ortho, Orthopedics, Sep. 2013, vol. 36, Issue 9, e1175-e1179.

Cwikiel W et al, "Electrolytic Stents to Inhibit Tumor Growth. An experimental study in vitro and in rats," Acta Radiologica, Informa Healthcare, GB, vol. 34, No. 3, May 1, 1993 (May 1, 1993), pp. 258-262.

International Search Report and the Written Opinion of the International Searching Authority issued in PCT/US2017/060947, dated Jan. 31, 2018.

\* cited by examiner

DRUG-FILLED STENTS WITH FILAMENTS FOR INCREASED LUMEN SURFACE AREA AND METHOD OF MANUFACTURE THEREOF

CROSS REFERENCE TO RELATED APPLICATIONS

This application claims the benefit under 35 U.S.C. § 119(e) of the filing date of U.S. Provisional Application No. 62/420,473 filed Nov. 10, 2016, the contents of which are incorporated by reference herein, in their entirety.

FIELD OF THE INVENTION

The present invention relates to drug-filled stents and methods of manufacturing drug-filled stents. More particularly, the present invention relates to drug-filled stents with an increased lumen surface area to promote tissue in-growth and methods of manufacture thereof.

BACKGROUND OF THE INVENTION

Drug-eluting implantable medical devices, such as stents, have become popular for their ability to perform their primary function, i.e., providing structural support to a body vessel, and their ability to medically treat the area in which they are implanted.

For example, drug-eluting stents have been used to prevent restenosis in coronary arteries. Drug-eluting stents may administer active agents (also referred to herein as drugs) such as anti-inflammatory compounds that block local invasion/activation of monocytes, thus preventing the secretion of growth factors that may trigger vascular smooth muscle cell (VSMC) proliferation and migration. Other potentially anti-restenotic compounds include antiproliferative agents, such as chemotherapeutics, which include rapamycin and paclitaxel. Other classes of drugs such as anti-thrombotics, anti-oxidants, platelet aggregation inhibitors and cytostatic agents have also been suggested for anti-restenotic use.

Drug-eluting implantable medical devices may be coated with a polymeric material which, in turn, is impregnated with an active agent or a combination of active agents. Once the medical device is implanted at a target location, the active agent(s) is released from the polymer for treatment of the local tissues. The active agent(s) is released by a process of diffusion through the polymer layer for biostable polymers, and/or as the polymer material degrades for biodegradable polymers.

Controlling the rate of elution of a drug from the drug impregnated polymeric material is generally based on the properties of the polymer material. However, at the conclusion of the elution process, the remaining polymer material in some instances has been linked to an adverse reaction with the vessel, possibly causing inflammation or a small but dangerous clot to form. Further, drug impregnated polymer coatings on exposed surfaces of medical devices may flake off or otherwise be damaged during delivery, thereby preventing the drug from reaching the target site. Still further, drug impregnated polymer coatings are limited in the quantity of the drug to be delivered by the amount of a drug that the polymer coating can carry and the size of the medical devices. Controlling the rate of elution using polymer coatings is also difficult.

Stents with hollow, drug-filled structural members have been contemplated and developed. For example, U.S. Pat. No. 6,071,305 to Brown et al., generally discloses a stent formed of an elongated member in a spiral tube configuration. The elongated member includes a groove that can be filled with an active agent. Further, U.S. Pat. No. 9,283,305 to Birdsall et al., U.S. Application Publication No. 2011/0070358 to Mauch et al., U.S. Pat. No. 8,460,745 to Mitchell et al., and U.S. Pat. No. 9,119,736 to Thompson, each of which is herein incorporated by reference in its entirety, describe methods of forming and filling stents with hollow, drug-filled structural members from composite wires. There remains a need in the art for improvements of drug-filled stents.

BRIEF SUMMARY OF THE INVENTION

Embodiments hereof relate to a stent including a hollow wire formed into a stent pattern. The hollow wire includes an outer member, a lumen, at least one opening, and at least one filament. The outer member has an outer surface and an inner surface. The lumen extends longitudinally within the hollow wire. The at least one opening extends from the outer surface of the outer member to the lumen. The at least one filament extends longitudinally within the lumen. The at least one filament increases the amount of surface area available for tissue in-growth within the lumen.

Embodiments hereof also relate to a stent including a hollow wire formed into a stent pattern. The hollow wire includes an outer member, a lumen, at least one opening, and a plurality of filaments. The outer member has an outer surface and an inner surface. The lumen extends longitudinally within the hollow wire. The at least one opening extends from the outer surface of the outer member to the lumen. The plurality of filaments extends longitudinally within the lumen. Each filament of the plurality of filaments is spaced from adjacent filaments of the plurality of filaments, and the spacing between adjacent filaments of the plurality of filaments is configured to permit tissue in-growth between the adjacent filaments.

Embodiments hereof further relate to a method of forming a stent. A composite wire including an outer member, a core member, and at least one filament disposed within the core member is shaped into a stent pattern. Openings are provided through the outer member to the core member. The composite wire is processed to remove the core member without adversely affecting the outer member or the at least one filament.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements.

The following detailed description is merely exemplary in nature and is not intended to limit the invention or the application and uses of the invention. Although the description of embodiments hereof is in the context of drug-filled medical devices for delivering active agents within a body vessel, medical devices described herein can also be used in other parts of the body. Furthermore, the medical devices may not include active agents. Additionally, there is no intention to be bound by any expressed or implied theory presented in the preceding technical field, background, brief summary or the following detailed description.

Figure 1:
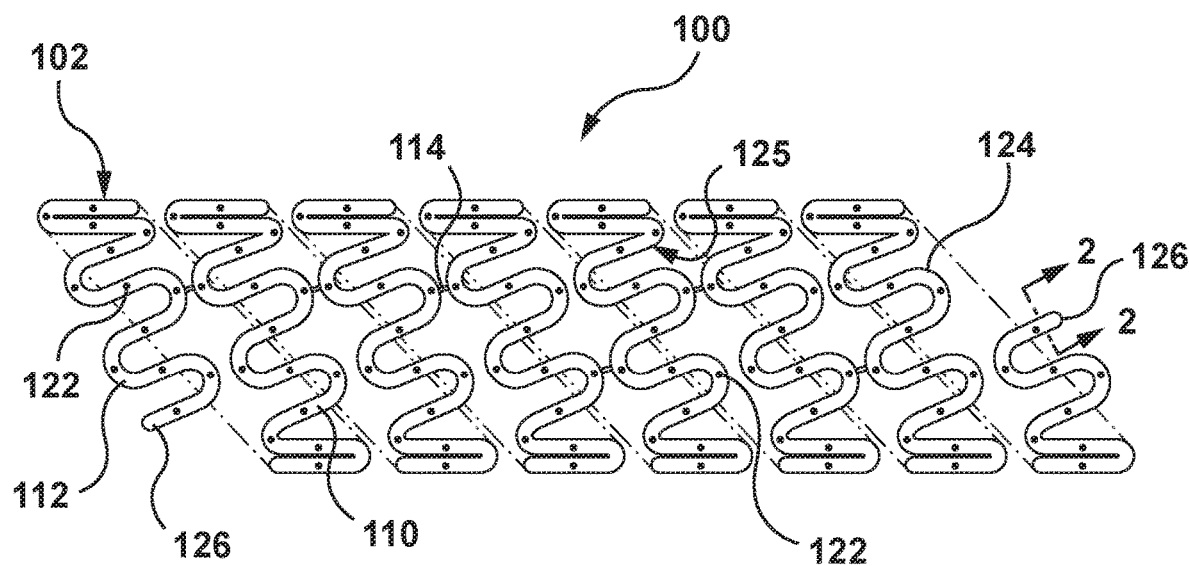
FIG. 1 is a schematic illustration of a stent in accordance with an embodiment hereof, wherein the stent is formed from a hollow wire with a plurality of filaments and an active agent disposed within the lumen of the hollow wire, the plurality of filaments forming an increased surface area within the lumen of the hollow wire.
Figure 2:
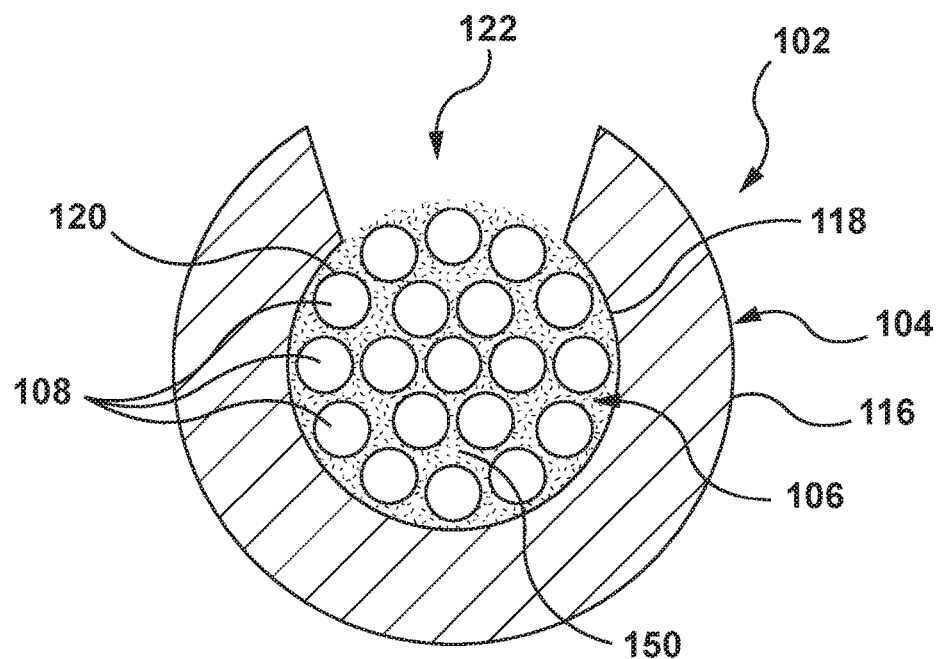
FIG. 2 is a cross-sectional view taken along line 2-2 of FIG. 1.

A stent 100 in accordance with an embodiment hereof is described herein and shown in FIGS. 1-2. The stent 100 is formed from a hollow wire 102. The hollow wire 102 includes an outer member 104, a lumen 106 defined by an inner surface 118 of the outer member 104 and extending longitudinally within the outer member 104. The hollow wire 102 further includes a plurality of openings 122 extending through the outer member 104 to the lumen 106, and a plurality of filaments 108 extending longitudinally within the lumen 106. The term "wire" as used herein means an elongated element or filament or group of elongated elements or filaments and is not limited to a particular cross-sectional shape or material, unless so specified.

In the embodiment of FIG. 1, the hollow wire 102 is formed into a series of generally sinusoidal waveforms including generally straight segments or struts 110 joined by bent segments or crowns 112. The waveform is helically wound to form the stent 100 into a generally tubular configuration. In the embodiment shown in FIG. 1, selected crowns 112 of longitudinally adjacent sinusoids may be joined by, for example, fusion points 114. However, the invention is not limited to the pattern or configuration shown in FIG. 1. The hollow wire 102 of the stent 100 can be formed into any pattern suitable for use as a stent. For example, and not by way of limitation, the hollow wire 102 of the stent 100 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is herein incorporated by reference in its entirety. Further, instead of a single length of hollow wire formed into a stent pattern, a plurality of hollow wires may be formed into a waveform and wrapped into individual annular elements. The annular elements may then be aligned along a common longitudinal axis and joined together to form a stent having a generally tubular configuration.

As described above and best shown in FIG. 2, the hollow wire 102 includes the outer member 104. The outer member 104 includes an outer surface 116 and the inner surface 118. In the embodiment of FIG. 2, the lumen 106 is defined or formed from the hollow portion of the outer member 104. The plurality of filaments 108 are disposed within the lumen 106 and extend longitudinally through one or more segments, sections or portions or for the full or entire length of the hollow wire 102. The plurality of filaments 108 are configured to increase the surface area within the lumen 106 for improved tissue in-growth as described in more detail below. The plurality of filaments 108 each have an outer surface 120. In the embodiment of FIG. 2, each filament 108 is generally spaced apart from each adjacent filament 108. In other words, each filament 108 is adjacent to, but not substantially in contact with any other filament 108. The spacing between adjacent filaments 108 is configured to permit and encourage tissue in-growth there-between. In addition, each filament 108 is also substantially spaced apart from the inner surface 118 of the outer member 104 so as to be adjacent to, but not in contact with the inner surface 118 of the outer member 104. The spacing may be selected to elicit a specific desired cell behavior or behavior set. While the hollow wire 102 is shown with eighteen (18) filaments 108, this is by way of example and not limitation, and the hollow wire 102 may include more or fewer filaments 108. Additionally, while each filament 108 is shown as having a generally circular cross-section, each filament 108 may have cross-sections of different shapes and/or sizes. The combination of one or more different shapes and/or sizes along one or more segments of each of the filaments 108 and/or between each of the filaments 108 may be selected to encourage preferred tissue in-growth of one or more cell types having one or more desired cell behaviors at one or more select locations of the stent 100. Further, although the hollow wire 102 is shown as generally having a circular cross-section along the entire length of the hollow wire 102, the hollow wire 102 may be generally elliptical or rectangular in cross-section. In some embodiments, the cross-sectional shape and/or size can vary along one or more segments of the hollow wire 102.

Although the plurality of filaments 108 have been described herein as extending the entire or full length of the hollow wire 102, this is by way of example and not limitation. It will be understood that the plurality of filaments 108, and more precisely each filament 108 of the plurality of filaments 108 may extend a distance or length less than the entire or full length of the hollow wire 102. Additionally, each filament 108 may start and stop along the length of the hollow wire 102 to form segments along the length of the hollow wire 102. Further, the segments of the plurality of filaments 108 may be positioned at select portions or locations of the stent 100 such as one or more crowns 112, one or more struts 110, or any combination thereof. In another embodiment, the segments of the plurality of filaments 108 may be positioned at the end portions of the stent 100. Positioning of the segments of the plurality of filaments 108 at select locations of the stent 100 may be utilized to encourage preferred tissue in-growth having one or more desired cell behaviors in select locations. The positioning of the segments of the plurality of filaments 108 at select locations of the stent 100 in combination with the selection of one or more shapes and/or sizes along one or more segments of each of the filaments 108 can be selected to create the desired amount of space between adjacent filaments 108 to selectively encourage preferred tissue in-growth of one or more cell types having one or more desired cell behaviors at one or more select locations of the stent 100.

Figure 3A:
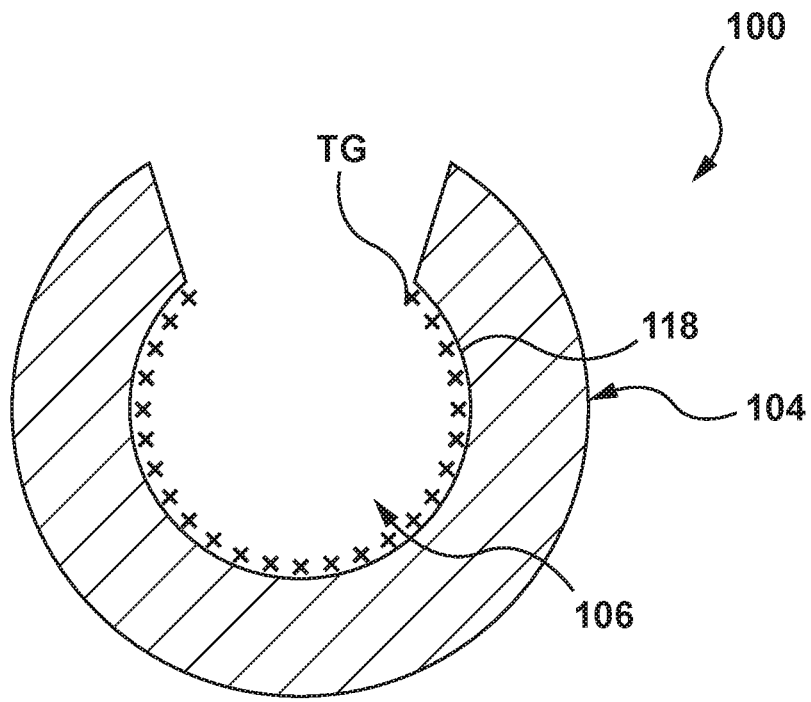
FIG. 3A is also a cross-sectional view of the hollow wire of FIG. 1, wherein the plurality of filaments and the active agent have been omitted to illustrate a surface area within a lumen without the plurality of filaments.
Figure 3B:
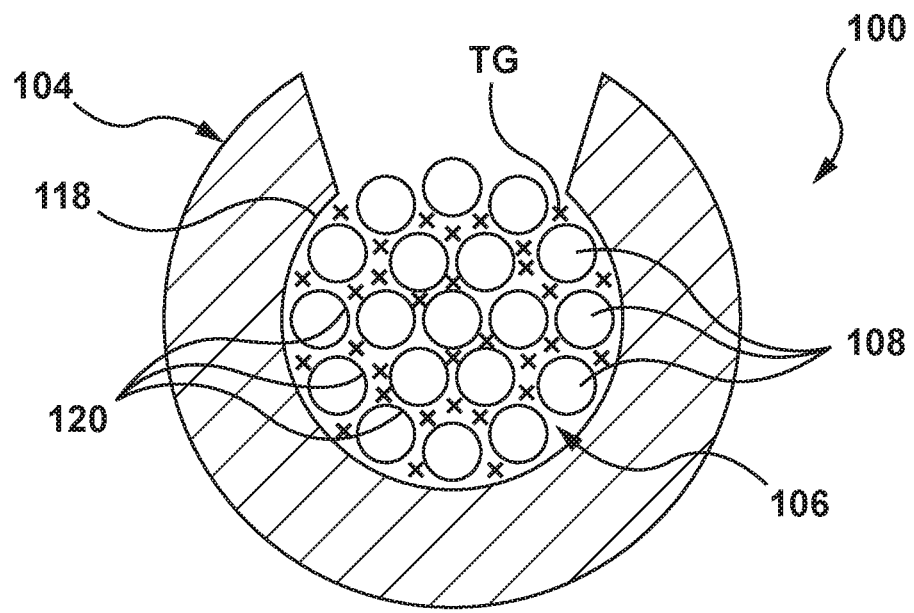
FIG. 3B is a cross-sectional view of the hollow wire of FIG. 1, wherein the plurality of filaments is shown to illustrate the increased surface area within the lumen with the plurality of filaments and to illustrate the tissue growth interspersed between the plurality of filaments after the active agent has eluted in situ.

FIGS. 3A and 3B illustrate the stent 100 without and with the plurality of filaments 108, respectively, and are included herein to illustrate the increase in the surface area within the lumen 106 with the plurality of filaments 108. Referring to FIG. 3A, when the plurality of filaments 108 are not present, the surface area available for tissue in-growth within the lumen 106 is only the inner surface 118 of the outer member 104. Stated another way, tissue TG may attach to the stent 100 within the lumen 106 only along the inner surface 118 of the outer member 104. However, as shown in FIG. 3B, when the plurality of filaments 108 are present, the surface area available for tissue in-growth within the lumen 106 includes both the inner surface 118 of the outer member 104 and the outer surface 120 of each filament 108. Thus, tissue TG may attach to the stent 100 within the lumen 106 along both the inner surface 118 of the outer member 104 and the outer surface 120 of each filament 108. Accordingly, the plurality of filaments 108 increases the surface area available for tissue in-growth within the lumen 106 of the stent 100 as will be described in more detail herein.

In the embodiment of FIG. 2, a biologically or pharmacologically active agent 150 (hereafter referred to as "active agent 150" for simplicity) is deposited within the lumen 106 and around the plurality of filaments 108 of the hollow wire 102. In the embodiment of FIG. 2, the plurality of openings 122 provide access to the lumen 106 to permit the active agent 150 to be released from the lumen 106. Further, the plurality of openings 122 provide access to the lumen 106 to permit tissue in-growth into the lumen 106 after the active agent 150 has been released from the lumen 106. The plurality of openings 122 may be sized and shaped as desired to control both the elution rate of the active agent 150 from the lumen 106 and to control the in-growth of cells into the lumen 106 of the stent 100. Larger sized openings 122 generally permit a faster elution rate and a faster in-growth rate and smaller sized openings 122 generally provide a slower elution rate and a slower in-growth rate. The size and/or quantity of the plurality of openings 122 may be varied along the stent 100 in order to vary both the quantity and/or rate of the active agent 150 being eluted from stent 100 and the in-growth of cells into the lumen 106 at different portions of stent 100. The plurality of openings 122 may be, for example and not by way of limitation, 10-40 μm in diameter. While shown in FIG. 1 with the plurality of openings 122 on an outwardly facing or abluminal surface 124, this is by way of example and not limitation, and the plurality of openings 122 may be provided on the abluminal surface 124 and/or on an inward facing or luminal surface 125, or may be provided anywhere along the circumference of the hollow wire 102.

As used herein, a biologically or pharmacologically "active agent" may include, but is not limited to, antineoplastic, antimitotic, anti-inflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other active substances or agents that may be used include nitric oxide, alpha-interferon, genetically engineered epithelial cells, and dexamethasone. In other examples, the active substance is a radioactive isotope for implantable device usage in radioactive procedures. Examples of radioactive isotopes include, but are not limited to, phosphorus ($P^{32}$), palladium ($Pd^{103}$), cesium ($Cs^{131}$), Iridium ($I^{192}$) and iodine ($I^{125}$). While the preventative and treatment properties of the foregoing active substances or agents are well-known to those of ordinary skill in the art, the substances or agents are provided by way of example and are not meant to be limiting. Other active substances are equally applicable for use with the disclosed methods and compositions. Further, a carrier may be used with the biologically or pharmacologically active agent. Examples of suitable carriers include, but are not limited to, ethanol, acetone, tetrahydrofuran, dymethylsulfoxide, a combination thereof, or other suitable carriers known to those skilled in the art. Still further, a surfactant may be formulated with the drug and the solvent to aid elution of the drug.

While described herein with the active agent 150 within the lumen 106, this is not meant to be limiting, and in an alternative embodiment, the lumen 106 may not contain the active agent 150. When the active agent 150 is not utilized, the plurality of openings 122 provide access to the lumen 106 only to permit tissue in-growth into the lumen 106. Accordingly, in such an embodiment, the plurality of openings 122 are sized and shaped to control only the in-growth of cells into the lumen 106 of the stent 100.

The ends 126 of the hollow wire 102 may be closed by crimping excess material of the hollow wire 102 to close the lumen 106. The ends 126 may also be closed by not removing a core member during the method of manufacture thereof, described in more detail below, from the ends 126. In the embodiment of FIG. 2, with the active agent 150 disposed within the lumen 106, closing the ends 126 prevents the active agent 150 from prematurely releasing from the ends 126. However, closing the ends 126 is not required as the active agent 150 may be dried, provided within a polymer matrix, enclosed within a liner (not shown in FIGS. 1-2), or otherwise protected from premature release from the ends 126. Further, the ends 126 may be welded, crimped or otherwise connected to other portions of the hollow wire 102 such that the ends 126 are not free ends.

When the stent 100 is deployed within a vessel, the active agent 150 elutes from the lumen 106 of the stent 100. Once the active agent 150 has been eluted, cells originating from the vessel migrate through the plurality of openings 122 and into the lumen 106. The cells attach or couple to the surfaces within the lumen 106. More specifically, the cells grow or fill the spaces between adjacent filaments 108 and couple to the inner surface 118 of the outer member 104 and to the outer surface 120 of each filament 108 as shown in FIG. 3B described above. Once attached thereto, the cells grow or colonize and form an extracellular matrix within the lumen 106 of the stent 100 to couple the stent 100 to the vessel. The spaces between the plurality of filaments 108 are all in fluid communication with each other in order to permit tissue in-growth between and around each individual filament 108. The increased surface area available within the lumen 106 with the plurality of filaments 108 permits more cells to couple to the stent 100, and thus more firmly anchors the stent 100 to the vessel. The improved mechanical integration, or coupling of the stent 100 to the vessel may offer clinical benefit in reducing micro-damage to the tissue surrounding the stent 100 during biomechanical motion of the vessel, such as the repetitive constriction and dilation of the vessel due to cardiac pressure differentials of the cardiac cycle. The term "micro-damage," as used herein, means tissue damage due to the relative movement between a generally rigid stent and a generally flexible vessel. Further, the term "biomechanical motion," as used herein means the motion or movement of a vessel. For example, and not by way of limitation, biomechanical motion includes the repetitive constriction and dilation of a body vessel due to cardiac pressure differentials of the cardiac cycle.

In embodiments without the active agent 150, when the stent 100 is deployed within a vessel, the cells of the vessel adjacent the plurality of openings 122 migrate through the plurality of openings 122 and into the lumen 106 to couple the stent 100 to the vessel as previously described.

Figure 4:
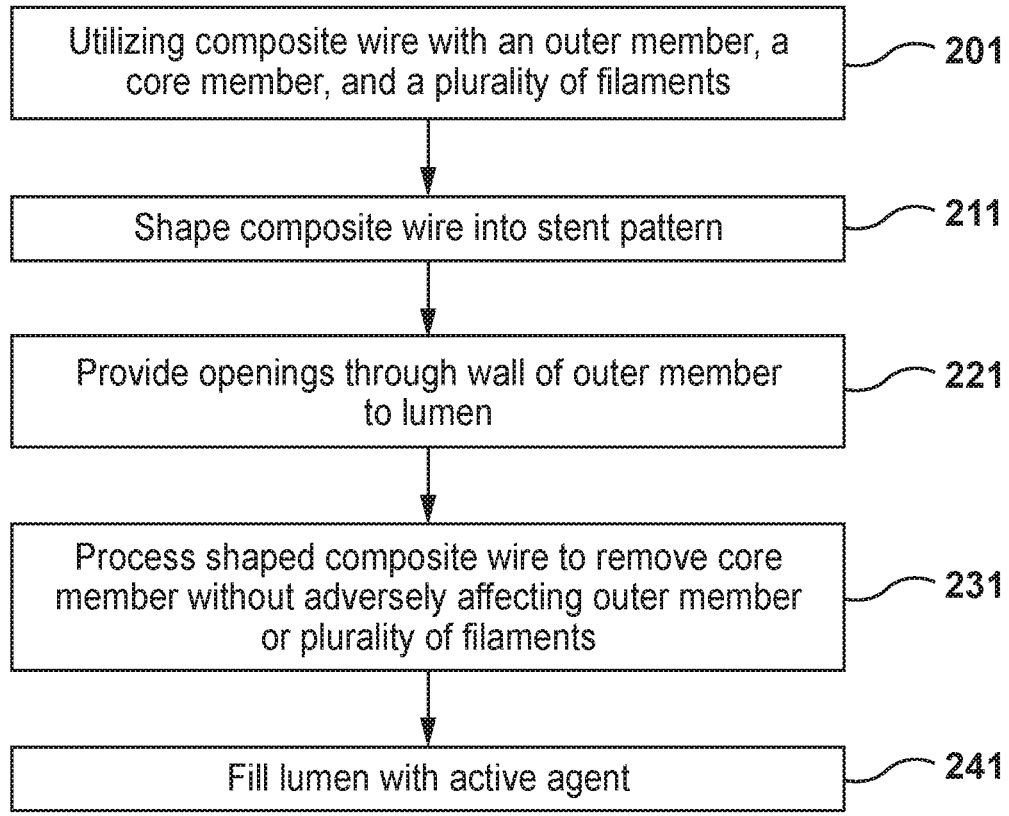
FIG. 4 is flow chart illustrating an embodiment of a method of forming the stent of FIG. 1.

FIGS. 4-8 show a method for forming a stent from a hollow wire, such as the stent 100, in accordance with an embodiment hereof. As shown in FIG. 4, step 201 is to utilize a composite wire 130 having the outer member 104, the plurality of filaments 108, and a core member 128, shown schematically in FIG. 5 and in cross-section in FIG. 6. The outer member 104 and the plurality of filaments 108 form the hollow wire 102 of the stent 100 described above with respect to FIGS. 1-2 after processing thereof to form the stent 100. The composite wire 130 may be formed by any method known in the art, for example and not by way of limitation, a co-drawing process, extrusion, cladding, or any other suitable method. Stated another way, the composite wire 130 may be formed by methods of forming composite wires known to those skilled in the art. Examples of composite wires and methods of forming composite wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is herein incorporated by reference in its entirety.

The outer member 104 may be any material that is suitable to be used as a stent. More particularly, the requirements for the material of the outer member 104 are that it be biocompatible, sufficiently resilient to be used as a stent, and that it survives the process for eliminating the core member 128, as described in more detail below. For example, and not by way of limitation, the outer member 122 may be a cobalt-chromium alloy. As used herein, the term "cobalt-chromium" alloy includes alloys with cobalt and chromium. Generally, materials such as, but not limited to, cobalt-nickel-chromium alloys ("MP35N" and "MP20N") and chromium-nickel-tungsten-cobalt alloys ("L605") and cobalt-chromium-nickel-molybdenum alloys ("ELGILOY") are the types of materials included in the term "cobalt-chromium alloys" as used herein.

Similarly, the plurality of filaments 108 may be any material that it is biocompatible, is sufficiently resilient to be used as a stent, and that survives the process for eliminating the core member 128. In an embodiment hereof, the plurality of filaments 108 may be a radiopaque material to permit the stent 100 to be visible under X-ray or fluoroscopic imaging equipment when the outer member 104 is made of a material that is difficult to visualize under X-ray or fluoroscopic imaging equipment. Thus, selection of the plurality of filaments 108 depends on the material of the core member 128, the process selected for removing the core member 128, and the desired radiopacity of the plurality of filaments 108.

Figure 5:
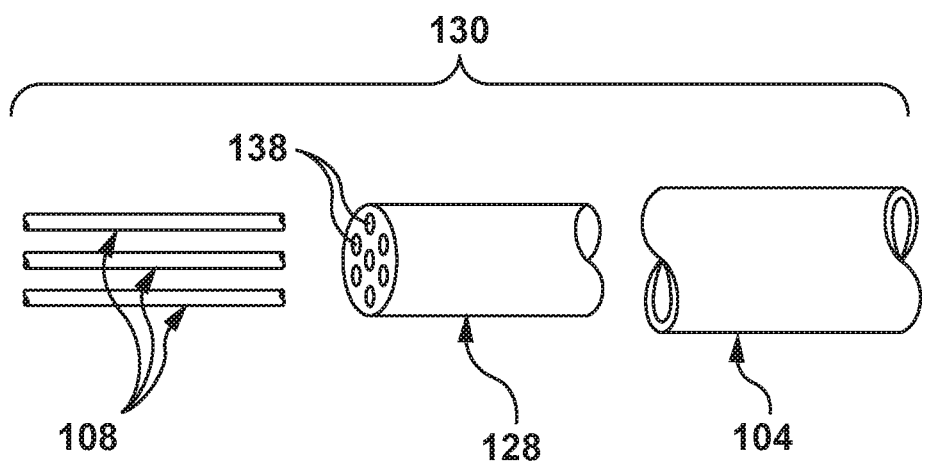
FIG. 5 is a schematic illustration of a composite wire which may be utilized for forming a stent in the method of FIG. 4, the composite wire including an outer member, a core member, and a plurality of filaments.
Figure 6:
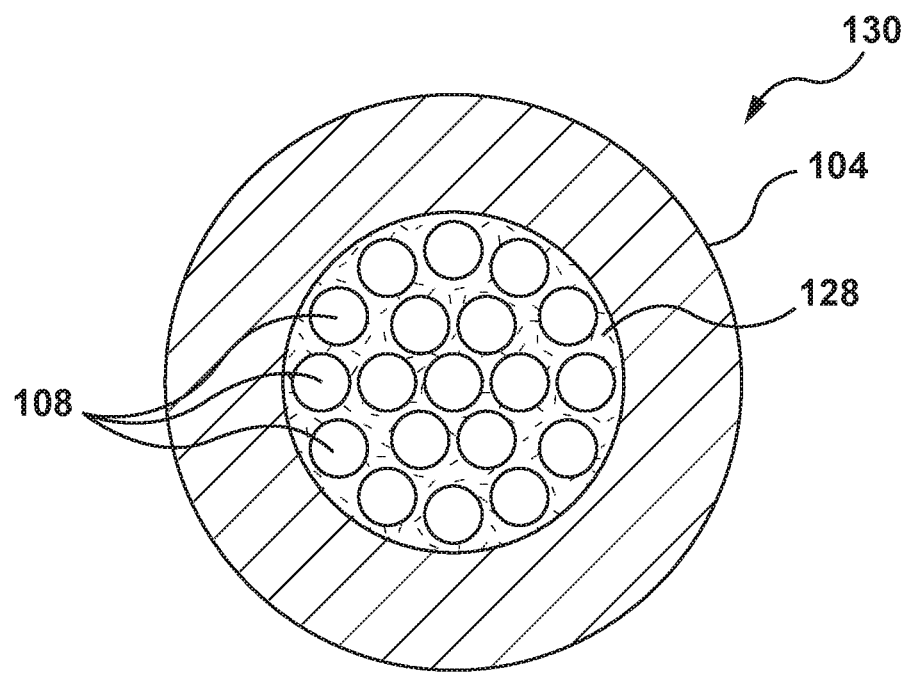
FIG. 6 is a cross-sectional view of the composite wire of FIG. 5 at a step in the method of FIG. 4, wherein the plurality of openings has not been provided and the core member has not been processed for removal.

The core member 128 is a sacrificial material that is removed without damaging the plurality of filaments 108 or the outer member 104. In the embodiment of FIGS. 4-8, the core member 128 includes a plurality of longitudinal bores 138, as shown in FIG. 5. Each bore 138 may be formed by methods such as, but not limited to mechanical laser cutting, drilling, etching, or any other suitable method. A single filament 108 is disposed within each bore 138. The inner diameter of each bore 138 is slightly greater than the outer diameter of each filament 108. The term "slightly greater," as used herein means that the inner surface of each bore 138 has a larger cross-section than the cross-section of the corresponding filament 108 such that the corresponding filament 108 may slide or be disposed within the bore 138. The placement of the longitudinal bores 138 through the core member 128 determines the spacing between or pattern of the plurality of filaments 108 within hollow wire 102, which in turn dictates the amount of tissue in-growth and specific desired cell behavior as previously described in more detail above. Stated another way, the core member 128 and the longitudinal bores 138 essentially form a template that dictates the placement of the plurality filaments 108 within the lumen 106 of the hollow wire 102. After the plurality of filaments 108 are disposed within the core member 128, the core member 128 and the plurality of filaments 108 are collectively disposed within the outer member 104. The outer member 104, the core member 128 and the plurality of filaments 108 then undergo a process such as a co-drawing process to form the composite wire 130, as shown in FIG. 6.

In a non-limiting example, the outer member 104 is made of MP35N, the plurality of filaments 108 is made of tantalum, and the core member 128 is made of silver. In the non-limiting example, the process to remove the core member 128 is exposing the core member 128 to nitric acid. Other examples of material combinations of the outer member 104, the plurality of filaments 108, the core member 128, and the removal method are provided below in chart form.

While described herein with a boring and co-drawing process, this is by way of example and not limitation. In another embodiment, the composite wire 130 with the plurality of filaments 108 may be formed in a combination process such as the process utilized for manufacturing superconducting filaments. Examples of composite filaments and methods of forming composite filaments can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which has been previously incorporated by reference herein.

Referring back to FIG. 4, step 211 is to shape the composite wire 130 into the stent pattern. As discussed above, the stent pattern can be the pattern shown in FIG. 1 or any other suitable pattern formed from a wire. Further, although the order of all the steps is not critical, step 211 should be performed prior to removing the core member 128, as explained below. The step of shaping the composite member 130 into the stent pattern does not have to include shaping the composite member 130 into the final stent pattern. For example, the step 211 of shaping the composite member 130 into a stent pattern may include only forming the struts 110 and the crowns 112 with the composite wire 130. Shaping the composite wire 130 into the stent pattern while the core member 128 is disposed within the outer member 104 helps prevent kinking or other deformations from occurring in the outer member 104. Shaping the composite wire 130 into the stent pattern shown in FIG. 1 generally includes the steps of forming the composite wire 130 into a waveform pattern followed by wrapping the waveform pattern around a mandrel, as known to those skilled in the art. The end result is a helical stent pattern formed onto a mandrel. Selected crowns 112 of the waveform pattern may then be fused together and the stent may be removed from the mandrel. In addition to the technique described above, step 211 of shaping the composite wire 130 into the stent pattern can be performed with techniques known to those skilled in the art. For example, and not by way of limitation, forming the composite wire 130 into a waveform can be achieved using techniques described in U.S. Application Publication No. 2010/0269950 to Hoff et al. and U.S. Pat. No. 9,296,034 to Costa et al., each of which is herein incorporated by reference in its entirety, and U.S. Application Publication No. 2011/0070358 to Mauch et al., previously incorporated by reference. Other techniques understood by persons skilled in the art could also be used.

Figure 7:
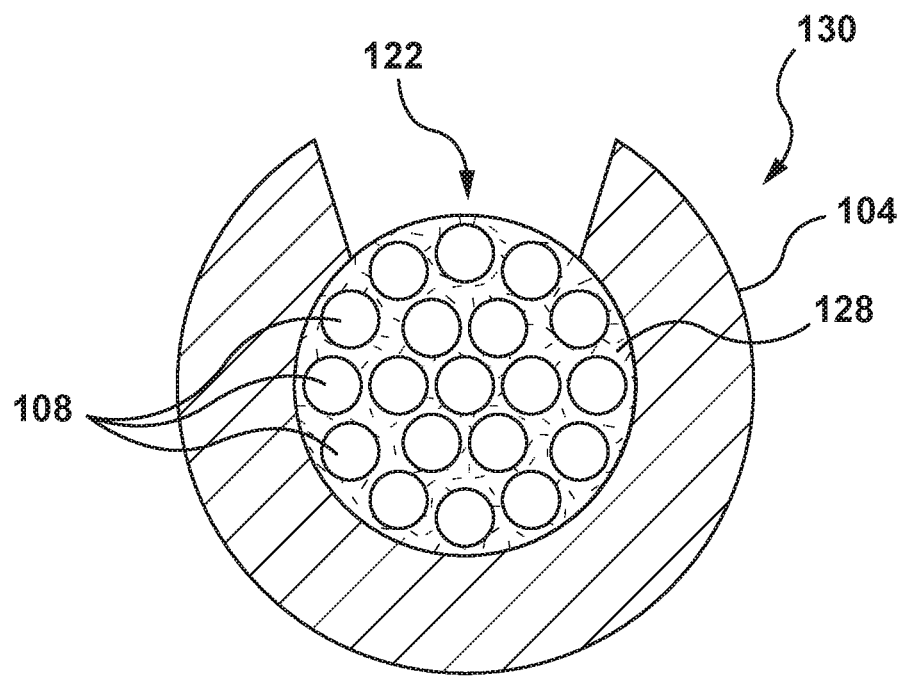
FIG. 7 is a cross-sectional view of the composite wire of FIG. 5 at a step in the method of FIG. 4, wherein the plurality of openings has been provided but the core member has not been processed for removal.
Figure 8:
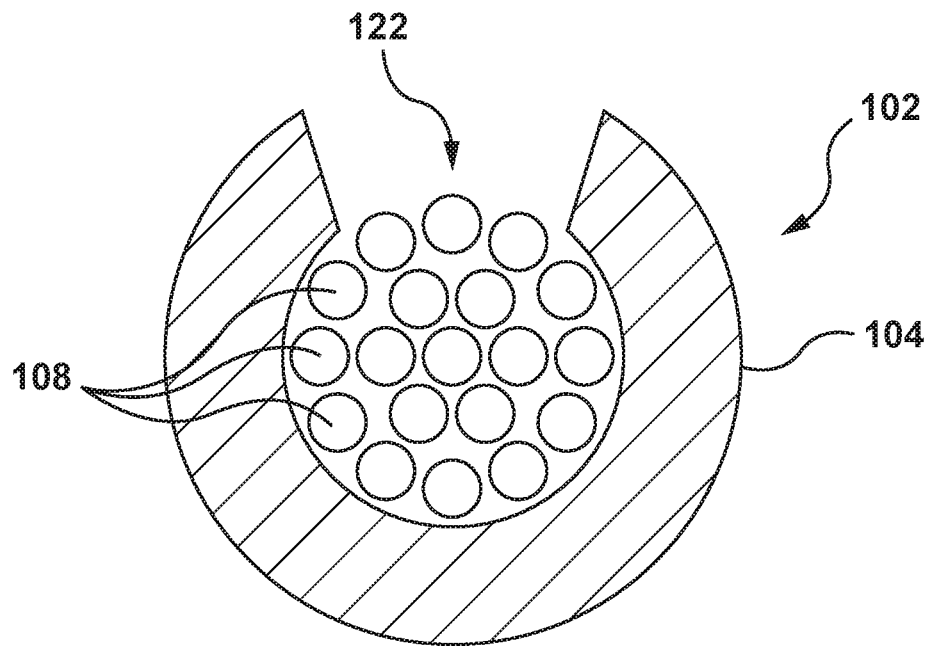
FIG. 8 is a cross-sectional view of the composite wire of FIG. 5 at a step in the method of FIG. 4, wherein the plurality of openings has been provided and the core member has been removed.

Step 221, shown in FIG. 4 as well as FIG. 7, is to provide the plurality of openings 122 through the outer member 104. The plurality of openings 122 may be laser cut, drilled, etched, or otherwise provided through the outer member 104. Step 221 is not required to be performed after step 211 or before step 231. However, it is preferred for step 221 to be performed before step 231 as the plurality of openings may be utilized as access to the core member 128 for processing, as explained in more detail below. If step 221 is performed after step 211, a cross-section of the composite wire 130 will include the outer member 104, the plurality of filaments 108, the core member 128, and one or more opening(s) 122 as shown in FIG. 7.

Step 231 is to remove the core member 128 from the lumen 106 of the outer member 104 without adversely affecting the outer member 104 or the plurality of filaments 108, such as by chemical etching. Step 231 can be performed by any suitable process for removing the core member 128 while preserving the outer member 104 and the plurality of filaments 108. In particular, exposing the composite wire 130 formed from an outer member 104 of MP35N, a plurality of filaments 108 of tantalum (Ta), and a core member 128 of silver (Ag) to nitric acid (NaNO3) causes the nitric acid (NaNO3) to react with the silver (Ag) core member 128 to form nitrogen monoxide (NO), silver nitrate (AgNO3), and water (H2O), which can be removed from the lumen 106. Nitric acid (NaNO3) reacts similarly with a core member 128 made from copper (Cu). However, nitric acid (NaNO3) does not react with an outer member 104 formed of MP35N or the plurality of filaments 108 formed of tantalum (Ta) described above. Accordingly, after step 231 is completed, the outer member 104 and the plurality of filaments 108 remain, and the core member 128 has been removed, leaving the cross-sectional structure shown in FIG. 8. As noted above, the plurality of openings 122 do not need to be formed prior to the step of removing the core member 128 as long as there is a way to expose the core member 128 to the etchant. For example, the ends 126 of the wire may be open or temporary ports may for formed through the outer member 104 to expose the core member 128 to the etchant.

Although a particular embodiment of the outer member 104 made from MP35N, the plurality of filaments 108 made from tantalum, the core member 128 made from silver, and a nitric acid etchant has been described, those skilled in the art would recognize that other combinations of materials and etchants could be utilized. For example, and not by way of limitation, the combination of materials and etchants described in the chart below may be utilized. Further, other materials and methods for removing core members may be used, as described, for example, in U.S. Application Publication No. 2011/0008405 to Birdsall et al. and U.S. Application Publication No. 2011/0070358 to Mauch et al., each of which has been previously incorporated by reference.

| Etchant | Outer Member | Intermediate Member | Core Member |
| --- | --- | --- | --- |
| Xenon-difluoride | Cobalt-chromium alloys (MP35N, MP20N, L605, ELGILOY) | Pt20Ir, Pt10Ir | Tantalum, tungsten, molybdenum, niobium, rhenium, carbon, germanium, silicon, Ta—2.5W |
| Nitric Acid, sulfuric acid | Cobalt-chromium alloys (MP35N, MP20N, L605, ELGILOY) Nitinol, Titanium, Titanium alloys | Tantalum, Ta—2.5W | Copper |
| Nitric Acid | Cobalt-chromium alloys (MP35N, MP20N, L605, ELGILOY) Nitinol, Titanium, Titanium alloys | Tantalum, Ta—2.5W | Silver |

| Etchant | Outer Member | Intermediate Member | Core Member |
|---|---|---|---|
| Water, salt water | Cobalt-chromium alloys (MP35N, MP20N, L605, ELGILOY), stainless steel, Nitinol, Titanium, Titanium alloys | Pt20Ir, Pt10Ir, Tantalum, Ta—2.5W | Zinc, Magnesium |
| Heat (separation via melt or sublimation) | Cobalt-chromium alloys (MP35N, MP20N, L605, ELGILOY), stainless steel, Nitinol, Titanium, Titanium alloys | Pt20Ir, Pt10Ir, Tantalum, Ta—2.5W | Zinc, Magnesium |
| Xenon difluoride Dilute HF | Cobalt-chromium alloys (MP35N, MP20N, L605, ELGILOY | Pt20Ir, Pt10Ir | Titanium, Titanium alloys |

Step 241 is to fill the lumen 106 of the outer member 104 with the active agent 150. The lumen 106 may be filled by methods known to those skilled in the art. Examples of methods of filling a drug eluting device can be found in U.S. Pat. No. 8,460,745 to Mitchell et al., U.S. Pat. No. 8,381,774 to Mitchell et al., U.S. Pat. No. 8,678,046 to Mitchell et al., U.S. Pat. No. 8,632,846 to Avelar et al., U.S. Pat. No. 8,828,474 to Avelar et al., U.S. Pat. No. 9,549,832 to Peterson et al., and U.S. Pat. No. 9,204,982 to Peterson et al., each of which is herein incorporated by reference in its entirety. In embodiments without the active agent 150, step 241 is omitted. In an embodiment, the spacing between the filaments 108 prior to disposing an active agent there between, or in the absence of an active agent prior to the ingrowth of tissue, may be maintained by one or more of the methods described below. More particularly, in an embodiment, the spacing between the filaments 108 may be maintained by securing the filaments 108 at the ends 126 of the hollow wire 102. In another embodiment, spacers (not shown) may be disposed at desired increments along the length of the hollow wire 102 during the initial wire draw to maintain spacing between the filaments 108. In yet another embodiment, the core member 128 may be only partially removed such that portions of the core member 128 remain at desired locations, such as but not limited to the crowns 112 of the hollow wire 102, to maintain the spacing of the filaments 108. However, since tissue-ingrowth may displace the filaments, it is not required to utilize one of the above-described methods for maintaining spacing between the filaments 108.

Figure 9:
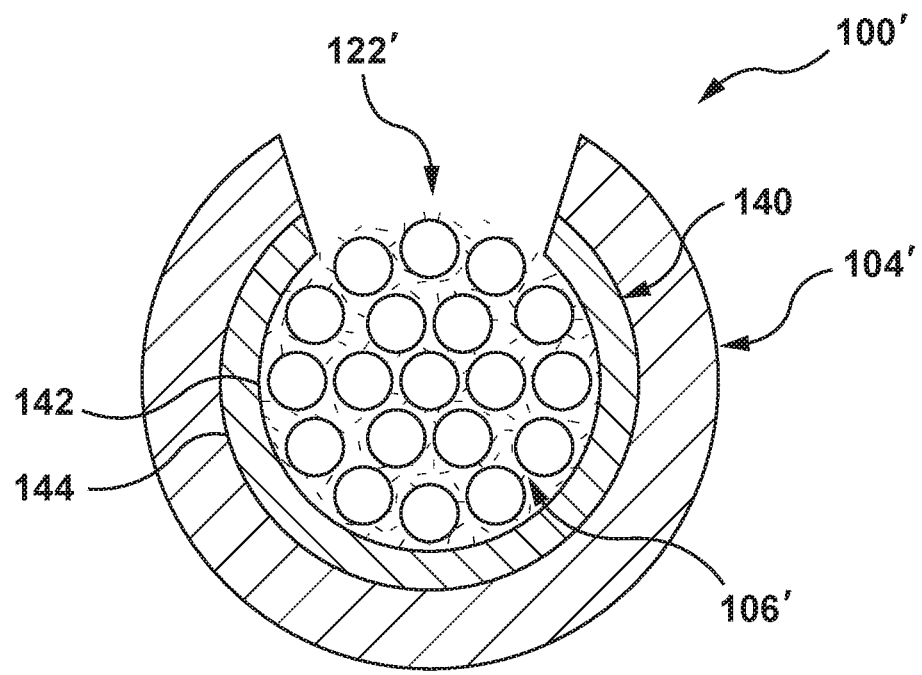
FIG. 9 is a cross-sectional illustration of a stent in accordance with another embodiment hereof, wherein the stent is formed from a hollow wire with a plurality of filaments and an active agent disposed within the lumen of the hollow wire, the plurality of filaments forming an increased surface area within the lumen of the hollow wire, and wherein the stent is formed from a tri-layer composite wire.

Although the stent 100 has been described herein as formed from a bi-layer composite wire with an outer member and a core member, this is not meant to be limiting, and it will be understood that in an alternate embodiment, a stent 100' may be formed from a tri-layer composite wire. As shown in FIG. 9, which is a cross-sectional view of the stent 100' formed of a tri-layer composite wire after processing to remove a core member, the tri-layer composite wire embodiment of the stent 100' generally includes an outer member 104', an intermediate member 140 lining at least a portion of the outer member 104', and the core member (not shown in FIG. 9, as the core member would be removed during processing as described above with respect to FIG. 4). The intermediate member 140 includes an inner surface 142 and an outer surface 144. In this embodiment, a lumen 106' is defined by the inner surface 142 of the intermediate member 140 and at least one opening 122' is disposed through the outer member 104' and the intermediate member 140 to the lumen 106'. The intermediate member 140 may be formed of a radiopaque material to permit the stent 100' to be visible under X-ray or fluoroscopic imaging equipment when the outer member is made of a material that is difficult to visualize under X-ray or fluoroscopic imaging equipment.

While various embodiments according to the present invention have been described above, it should be understood that they have been presented by way of illustration and example only, and not limitation. Various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent comprising:
a hollow wire formed into a stent pattern, wherein the hollow wire includes:
an outer member having an outer surface and an inner surface;
an intermediate member lining at least a portion of the inner surface of the outer member, the intermediate member having an outer surface and an inner surface;
a lumen extending longitudinally within the hollow wire, wherein the lumen is defined by the inner surface of the intermediate member and extends longitudinally within the intermediate member;
at least one opening disposed through the outer member to the lumen, wherein the at least one opening is disposed through the outer member and the intermediate member to the lumen; and
at least one filament extending longitudinally within the lumen,
wherein the at least one filament increases the amount of surface area available for tissue in-growth within the lumen.

2. The stent of claim 1, wherein the at least one filament extends a full length of the hollow wire.

3. The stent of claim 1, wherein the at least one filament has a circular cross-section.

4. The stent of claim 1, further comprising a plurality of filaments extending longitudinally within the lumen, wherein each filament of the plurality of filaments is spaced from an adjacent filament of the plurality of filaments.

5. The stent of claim 4, wherein the plurality of filaments includes at least ten filaments.

6. The stent of claim 1, wherein the outer member is formed from a cobalt-chromium alloy.

7. The stent of claim 6, wherein the at least one filament is formed from tantalum.

8. The stent of claim 1, wherein the intermediate member is formed from a radiopaque material.

9. The stent of claim 1, further comprising a biologically or pharmacologically active agent disposed in the lumen.

10. A stent comprising:
a hollow wire formed into a stent pattern, wherein the hollow wire includes:

an outer member having an outer surface and an inner surface;

a lumen extending longitudinally within the hollow wire;

a plurality of openings, wherein each opening is disposed through the outer member to the lumen and wherein each opening of the plurality of openings is spaced from adjacent openings of the plurality of openings; and a plurality of filaments extending longitudinally within the lumen, wherein each filament of the plurality of filaments is spaced from adjacent filaments of the plurality of filaments, and wherein no material is disposed within spacing between adjacent filaments and spacing between adjacent filaments of the plurality of filaments is configured to permit tissue in-growth between the adjacent filaments.

11. The stent of claim 10, wherein each filament of the plurality of filaments extends a full length of the hollow wire.

12. The stent of claim 10, wherein each filament of the plurality of filaments has a circular cross section.

13. A stent comprising:
a hollow wire formed into a stent pattern, wherein the hollow wire includes:
an outer member having an outer surface and an inner surface;
a lumen extending longitudinally within the hollow wire;
at least one opening disposed through the outer member to the lumen; and
a plurality of filaments extending longitudinally within the lumen, wherein each filament of the plurality of filaments is spaced from adjacent filaments of the plurality of filaments, and wherein the plurality of filaments includes at least ten filaments, and
wherein spacing between adjacent filaments of the plurality of filaments is configured to permit tissue in-growth between the adjacent filaments.

14. The stent of claim 13, wherein each filament of the plurality of filaments extends a full length of the hollow wire.

15. The stent of claim 13, wherein each filament of the plurality of filaments has a circular cross section.

16. The stent of claim 13, wherein the lumen is defined by the inner surface of the outer member and extends longitudinally within the outer member.

17. The stent of claim 13, wherein the stent further comprises:
an intermediate member lining at least a portion of the inner surface of the outer member, the intermediate member having an outer surface and an inner surface, and
wherein the lumen is defined by the inner surface of the intermediate member and extends longitudinally within the intermediate member, and
wherein the at least one opening is disposed through the outer member and the intermediate member to the lumen.

18. The stent of claim 13, further comprising a biologically or pharmacologically active agent disposed in the lumen between adjacent filaments of the plurality of filaments.

19. A stent comprising:
a hollow wire formed into a stent pattern, wherein the hollow wire includes:
an outer member having an outer surface and an inner surface;
a lumen extending longitudinally within the hollow wire, wherein the lumen is defined by the inner surface of the outer member and extends longitudinally within the outer member;
at least one opening disposed through the outer member to the lumen; and
a plurality of filaments extending longitudinally within the lumen, wherein each filament of the plurality of filaments is spaced from adjacent filaments of the plurality of filaments, and
wherein no material is disposed within spacing between adjacent filaments and the spacing between adjacent filaments of the plurality of filaments is configured to permit tissue in-growth between the adjacent filaments.

* * * * *